(12) United States Patent
Tamura et al.

(10) Patent No.: US 10,940,464 B2
(45) Date of Patent: Mar. 9, 2021

(54) CATALYST FOR PRODUCING ACRYLIC ACID AND METHOD FOR PRODUCING ACRYLIC ACID

(71) Applicant: NIPPON KAYAKU KABUSHIKI KAISHA, Tokyo (JP)

(72) Inventors: Kouichi Tamura, Yamaguchi (JP); Tatsuhiko Kurakami, Yamaguchi (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/332,514

(22) PCT Filed: Sep. 11, 2017

(86) PCT No.: PCT/JP2017/032610
§ 371 (c)(1),
(2) Date: Mar. 12, 2019

(87) PCT Pub. No.: WO2018/051933
PCT Pub. Date: Mar. 22, 2018

(65) Prior Publication Data
US 2019/0262806 A1    Aug. 29, 2019

(30) Foreign Application Priority Data
Sep. 14, 2016    (JP) .............................. JP2016-179885

(51) Int. Cl.
| B01J 23/888 | (2006.01) |
| B01J 21/04 | (2006.01) |
| B01J 37/00 | (2006.01) |
| B01J 37/04 | (2006.01) |
| B01J 37/08 | (2006.01) |
| C07C 51/235 | (2006.01) |
| B01J 33/00 | (2006.01) |
| C07B 61/00 | (2006.01) |

(52) U.S. Cl.
CPC .......... B01J 23/8885 (2013.01); B01J 21/04 (2013.01); B01J 23/888 (2013.01); B01J 33/00 (2013.01); B01J 37/00 (2013.01); B01J 37/0036 (2013.01); B01J 37/04 (2013.01); B01J 37/08 (2013.01); C07C 51/235 (2013.01); C07B 61/00 (2013.01)

(58) Field of Classification Search
CPC .... B01J 23/8885; B01J 23/88; B01J 23/8872; B01J 23/8873; B01J 23/8874; B01J 23/8875; B01J 23/8877; B01J 21/04; B01J 33/00; B01J 37/00; B01J 37/0036; B01J 37/04; B01J 37/08; B01J 23/22; B01J 23/28; C07C 51/235; C07B 61/00
USPC ................. 502/306–310, 312, 313, 316, 317
See application file for complete search history.

(56) References Cited

U.S. PATENT DOCUMENTS

| 4,176,234 | A | * | 11/1979 | Grasselli | ............ | B01J 23/8876 502/212 |
| 4,297,247 | A | * | 10/1981 | Krabetz | ................ | B01J 23/002 427/215 |
| 4,307,247 | A | * | 12/1981 | Shaw | .................... | C07C 51/377 502/304 |
| 5,446,004 | A | * | 8/1995 | Tenten | ................... | B01J 23/002 502/312 |
| 5,959,143 | A | | 9/1999 | Sugi et al. | | |
| 7,022,643 | B2 | * | 4/2006 | Yunoki | ................ | B01J 23/8885 502/179 |
| 7,109,372 | B2 | | 9/2006 | Hirao et al. | | |
| 7,211,692 | B2 | * | 5/2007 | Dieterle | ................ | C07C 51/252 562/532 |
| 7,220,698 | B2 | * | 5/2007 | Yunoki | .................. | B01J 23/002 502/312 |
| 8,877,964 | B2 | * | 11/2014 | Nakazawa | ............ | C07C 51/235 562/535 |
| 9,751,822 | B2 | * | 9/2017 | Kurakami | ............ | B01J 35/1038 |
| 2003/0109381 | A1 | | 6/2003 | Ohishi et al. | | |
| 2006/0128561 | A1 | | 6/2006 | Taniguchi | | |
| 2007/0021629 | A1 | * | 1/2007 | Stevenson | ............ | B01J 23/002 562/535 |
| 2007/0021630 | A1 | * | 1/2007 | Liang | .................... | B01J 23/002 562/535 |
| 2007/0038004 | A1 | * | 2/2007 | Shin | ....................... | B01J 23/002 562/537 |

(Continued)

FOREIGN PATENT DOCUMENTS

| EP | 0017000 A1 * | 10/1980 | .......... B01J 37/0223 |
| JP | 61-76436 | 4/1986 | |

(Continued)

OTHER PUBLICATIONS

English translation of PCT/JP2017/032610 Written Opinion. (dated 2017).*
International Search Report, dated Oct. 31, 2017 in corresponding International Application No. PCT/JP2017/032610, with English language translation.
Notification of Reasons of Refusal, dated Sep. 13, 2018 in corresponding Japanese Patent Application No. 2016-179885, with English language translation.

(Continued)

*Primary Examiner* — Patricia L. Hailey
(74) *Attorney, Agent, or Firm* — Wenderoth, Lind & Ponack, L.L.P.

(57) ABSTRACT

The present invention clarifies the characteristic of the hygroscopicity of the catalyst for producing acrylic acid and finds out a relationship between the water amount of the catalyst and the catalytic performance as the catalyst for producing acrylic acid, and provides an excellent catalyst. Provided is a catalyst for producing acrylic acid, which contains molybdenum and vanadium as essential active components, in which the amount of water contained in the catalyst is 0.01 mass % or more and 0.53 mass % or less.

2 Claims, No Drawings

(56) References Cited

U.S. PATENT DOCUMENTS

| | | | |
|---|---|---|---|
| 2008/0187467 A1* | 8/2008 | Dieterle | B01J 8/0285 422/187 |
| 2012/0065427 A1 | 3/2012 | Sudo et al. | |
| 2012/0071687 A1* | 3/2012 | Herzog | C07C 51/235 562/598 |
| 2013/0217915 A1 | 8/2013 | Nakazawa et al. | |
| 2014/0221683 A1* | 8/2014 | Welker-Nieuwoudt | B01J 23/30 562/535 |
| 2016/0244393 A1 | 8/2016 | Kurakami et al. | |

FOREIGN PATENT DOCUMENTS

| | | | | |
|---|---|---|---|---|
| JP | 2003 010695 | * | 1/2003 | B01J 27/199 |
| JP | 2003-10695 | | 1/2003 | |
| JP | 3786297 | | 6/2006 | |
| JP | 3883755 | | 2/2007 | |
| JP | 2008-155126 | | 7/2008 | |
| JP | 2012 148202 | * | 8/2012 | B01J 27/199 |
| JP | 2012-148202 | | 8/2012 | |
| JP | 2012 245433 | * | 12/2012 | B01J 27/199 |
| JP | 2012-245433 | | 12/2012 | |
| JP | 5680373 | | 3/2015 | |
| JP | 2015-96497 | | 5/2015 | |
| WO | 2004/062798 | | 7/2004 | |
| WO | 2004/062798 | * | 7/2007 | B01J 33/00 |
| WO | 2013/084258 | * | 6/2013 | B01J 23/88 |

OTHER PUBLICATIONS

Extended European Search Report dated Apr. 23, 2020 in corresponding European Patent Application No. 17850835.4.
Office Action dated Jul. 27, 2020 in corresponding Indian Patent Application No. 201917009863 with English-language translation.

* cited by examiner

CATALYST FOR PRODUCING ACRYLIC ACID AND METHOD FOR PRODUCING ACRYLIC ACID

TECHNICAL FIELD

The present invention relates to a catalyst for producing acrylic acid, a method for storing the same, and a method for producing acrylic acid.

BACKGROUND ART

Methods for producing acrylic acid using a fixed bed catalytic reactor are widely known. Most common methods include a method for producing acrolein-containing gas by using propylene as a raw material and partially oxidizing the propylene in a first stage reaction, and then producing acrylic acid by partially oxidizing the acrolein in a second stage reaction. For example, Patent Documents 1 to 3 disclose details of a catalyst for producing acrylic acid in the second stage reaction and a method for producing acrylic acid.

However, there is almost no description of a method for storing the catalyst, and particular ingenuity is not required for storage. The catalyst used for producing methacrylic acid from methacrolein, which is the similar reaction, is a chemical substance called a heteropoly acid, and the hygroscopicity thereof is widely known.

CITATION LIST

Patent Literature

Patent Document 1: Japanese Patent No. 3786297
Patent Document 2: Japanese Patent No. 3883755
Patent Document 3: Japanese Patent No. 5680373

SUMMARY OF INVENTION

Technical Problem

In the case of producing acrylic acid in an industrial reactor, in almost all cases, it is necessary to store the catalyst for several days to several months from the completion of production of the catalyst until the catalyst being filled in the reactor. Particularly, in the case of producing acrylic acid in a newly constructed industrial reactor and the like, the catalyst for spare use may be stored to prepare for emergency. In this case, the storage period of the catalyst may be 1 to 10 years. In case where the storage conditions are inappropriate, there is a possibility that problems such as failure to achieve the desired performance or failure to play a role for spare use may occur.

Nevertheless, little technical investigation concerning the method of storing the catalyst for producing acrylic acid have been made. It is not always clear as to what circumstances the catalyst should be stored in and what state the catalyst should be stored so as to achieve the desired catalytic performance, but it is common to rely on empirical rule. Then, the present invention clarifies the characteristic of the hygroscopicity of the catalyst for producing acrylic acid and finds out a relationship between the water amount of the catalyst and the catalytic performance as the catalyst for producing acrylic acid, and an object is to provide an excellent catalyst and an appropriate method for storing the same.

Solution to Problem

The present inventors made extensive investigations to the storage conditions of the catalyst for producing acrylic acid. As a result, the present inventors found out a catalyst capable of exhibiting the desired catalytic performance even after storage by setting the water amount of the catalyst during storage to a range of 0.01 mass % or more and 0.53 mass % or less, a method for storing the same, and a method for producing acrylic acid, thereby leading to accomplishment of the present invention.

That is, the present invention relates to:

(1) a catalyst for producing acrylic acid, comprising molybdenum and vanadium as essential active components, wherein an amount of water contained in the catalyst is 0.01 mass % or more and 0.53 mass % or less; and (2) a method for producing acrylic acid using the catalyst according to (1) above.

Advantageous Effects of Invention

According to the present invention, it is possible to provide a catalyst having a catalytic performance equivalent to that at the completion of production even after storage, and to produce acrylic acid using the catalyst.

DESCRIPTION OF EMBODIMENTS

Preferred embodiments will now be described in the practice of the present invention.

The catalyst according to the present invention is not particularly limited with respect to other metal components, as long as it contains molybdenum and vanadium as catalytically active components. When the composition of a preferred composite metal oxide as active components of the catalyst for producing acrylic acid is represented by formula, for example, it is represented by the following formula (1).

$$(Mo)_{12}(V)_a(W)_b(Cu)_c(Sb)_d(X)_e(Y)_f(Z)_g(O)_h \tag{1}$$

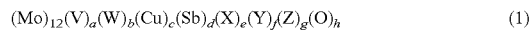

(In the formula, Mo, V, W, Cu, Sb, and O represent molybdenum, vanadium, tungsten, copper, antimony and oxygen, respectively; X represents at least one element selected from the group consisting of alkali metals and thallium; Y represents at least one element selected from the group consisting of magnesium, calcium, strontium, barium and zinc; and Z represents at least one element selected from the group consisting of niobium, cerium, tin, chromium, manganese, iron, cobalt, samarium, germanium, titanium and arsenic. In addition, a, b, c, d, e, f, g and h represent the atomic ratios of respective elements, and with respect to molybdenum atom 12, a represents $0<a\leq10$, b represents $0\leq b\leq10$, c represents $0<c\leq6$, d represents $0\leq d\leq10$, e represents $0\leq e\leq0.5$, f represents $0\leq f\leq1$, and g represents $0\leq g<6$. Further, h is the number of oxygen atoms necessary to satisfy the valences of the respective components.) As described in the formula, since the catalyst according to the present invention is essentially a catalyst having an isopolyacid crystal structure containing molybdenum and vanadium as essential active components, the effects of the present invention are not limited by other components.

In the catalyst according to the present invention, it is preferable to contain copper as an essential component in addition to molybdenum and vanadium, and in this case, the composition represented by the above formula (1) is preferred.

The catalyst according to the present invention can be obtained by calcinating the powder obtained by drying a mixture of a compound(s) containing a catalytically active component(s) and water, and then shaping the calcinated powder by a tumbling granulation method. Hereinafter, preferred embodiments will be described for respective steps.

Step a) Preparation

Raw materials used for preparing the catalytically active components are not particularly limited, and ammonium salts, nitrates, sulfates, acetates, oxides, chlorides and the like which are commonly used are used. Specific examples of the compounds include: molybdenum-containing compounds such as molybdenum trioxide, molybdic acid or a salt thereof; vanadium-containing compounds such as vanadium pentoxide, vanadyl sulfate, vanadic acid or a salt thereof; copper-containing compounds such as copper oxide, copper sulfate, copper nitrate, copper acetate, and copper molybdate; and antimony-containing compounds such as antimony trioxide, antimony pentoxide, antimony acetate, and antimony trichloride. In addition, examples of tungsten-containing compounds include tungstic acid or a salt thereof. In preparing the catalyst according to the present invention, first, an aqueous solution or an aqueous dispersion is prepared by mixing the above catalytically active component-containing compound(s) and water. (Hereinafter, unless otherwise specified, the aqueous solution or aqueous dispersion is collectively referred to simply as slurry solution.) In the present invention, it is preferable that the solvent forming the slurry solution is water. The content ratio of respective catalytically active component-containing compounds in the slurry solution is not particularly limited, as long as it falls within the range of the atomic ratio of the above formula (1). It is preferable to add respective component raw materials by dissolving or dispersing the same in water when adding respective component raw materials. The amount of the water to be used at that time is not particularly limited as long as it can completely dissolve the whole amount of the compounds to be used or mix the compounds uniformly. The amount of the water to be used is suitably decided in consideration of the drying step, the temperature and the like to be described below, and is usually 200 parts by mass or more and 2000 parts by mass or less with respect to 100 parts by mass of the total mass of the compounds. When the amount of the water is too small, the compounds cannot be completely dissolved or mixed uniformly. On the other hand, when the amount of the water is too large, an economic problem that the energy cost of the drying step increases or a problem that the drying is insufficient may occur.

Step b) Drying

Then, the uniform slurry solution obtained above is dried. The drying method is not particularly limited as long as it is a method capable of drying the slurry solution and obtaining powder having uniform components as a whole, and examples thereof include drum drying, freeze drying, and spray drying. Among them, spray drying is preferred in the present invention because the slurry solution can be dried from a slurry solution state to a powder state in a short time. The drying temperature in this case varies depending on the concentration of the slurry solution, the feeding speed and the like, but in general the temperature at the outlet of the drier machine is 85° C. or higher and 130° C. or lower. In addition, it is preferable to dry the slurry solution such that the average particle diameter of the dry powder obtained at this time becomes 20 μm or more and 60 μm or less.

Step c) Preliminary Calcination and Grinding

Next, the dried powder obtained above is preliminary calcinated at 200° C. or higher and 600° C. or lower, preferably 300° C. or higher and 450° C. or lower, for 1 hour or more and 15 hours or less, preferably 3 hours or more and 8 hours or less, according to need, and if necessary, the powder after preliminary calcination is ground to obtain preliminary calcinated granules.

Step d) Shaping

The catalyst according to the present invention is produced by carrying the granules prepared through the above steps on a spherical carrier to be coated having a diameter of 2.5 mm or more and 10 mm or less such as silicon carbide, alumina, mullite, and alundum by a tumbling granulation method and the like using a liquid binder component with a centrifugal acceleration of 0.5 G or more and 30 G or less. The tumbling granulation method is a method in which a carrier in the container is vigorously agitated by repeating a rotation motion and a revolution motion, for example, by rotating a disk at high speed in a device having a flat or uneven disk at the bottom of the fixed container, and a mixture of a liquid binder and the preliminary calcinated granules and, if necessary, a shaping auxiliary agent and a strength improver is added thereto so as to coat the carrier with the mixture. At this time, a catalyst having both catalytic performance and mechanical strength can be produced by setting the centrifugal acceleration to 0.5 G or more and 30 G or less. When the relative centrifugal acceleration in granulation is small, the mechanical strength is weak and the catalyst component peels off due to the filling operation into the reaction tube, making the carrying ratio of the active components nonuniform and increasing the pressure loss due to the peeled powder. Thus, a catalyst which cannot be used practically is obtained. When the relative centrifugal acceleration is large, the catalytic performance tends to decrease. When the relative centrifugal acceleration is more than 30 G, the catalytic active component may be peeled off during the granulation step, which is not preferable. The relative centrifugal acceleration can be calculated by the following equation.

$$\text{Relative centrifugal acceleration (G)} = 11.18 \times \text{bottom plate radius (m)} \times (\text{bottom[bottom plate rotational frequency (rpm)}]^2/10^8$$

The method for adding the liquid binder can be arbitrarily adopted, such as previously mixing the liquid binder with the above mixture, adding the liquid binder at the same time as adding the mixture into the fixed container, adding the liquid binder after adding the mixture, adding the liquid binder before adding the mixture, respectively dividing and adding simultaneously or alternately the mixture and the liquid binder, and adding the entire amount of the liquid binder by appropriately combining the above methods. In the method in which the mixture and the liquid binder are respectively divided and added alternately, for example, it is preferable to adjust the addition rate by using an auto-feeder or the like, such that a predetermined amount is carried on the carrier without adhesion of the mixture to the fixed container wall and aggregation of the mixture.

Examples of the liquid binder include water, ethanol, polyvinyl alcohol as a polymeric binder, silica sol aqueous solution as an inorganic binder. Alcohols such as diols and triols such as ethylene glycol and glycerin are preferred, and glycerin is particularly preferred. Alcohols may be used as they are, but it is effective to obtain a high performance catalyst by using the alcohols as an aqueous solution having a concentration of 10 mass % or more. The amount of the liquid binder to be used is usually 10 parts by mass or more and 50 parts by mass or less with respect to 100 parts by mass of the preliminary calcinated granules.

Specific examples of the carrier which can be used include spherical carriers having a diameter of 2.5 mm or more and 10 mm or less such as silicon carbide, alumina, mullite, and alundum. Of the carriers, a carrier having a porosity of 30% or more and 50% or less, a water absorptivity of 10% or more and 30% or less, a cumulative specific surface area measured by a mercury porosimeter of 0.1 $m^2$/g or more and 50 $m^2$/g or less, and a cumulative pore volume of 0.05 ml/g or more and 2 ml/g or less is preferably used. The preliminary calcinated granules to be added to the carrier are usually adjusted so as to satisfy the preliminary calcinated granules/(preliminary calcinated granules+carrier)=10 mass % or more and 75 mass % or less, preferably 15 mass % or more and 50 mass % or less.

Step e) Main Calcination

The shaped product obtained in this way can be calcinated (main calcination) again after shaping, to obtain a catalyst. The main calcination temperature is usually 250° C. or higher and 500° C. or lower, preferably 300° C. or higher and 450° C. or lower, and the main calcination time is 1 hour or more and 50 hours or less, preferably 3 hour or more and 8 hours or less.

The steps of producing the catalyst ends at the main calcination step, and the catalyst according to the present invention can exhibit the equivalent performance as the catalyst immediately after production, even after storage for a long period of time.

The catalyst according to the present invention can exhibit the equivalent performance as the catalyst immediately after production, even after storage for a long period of time, by adjusting the amount of water to 0.01 mass % or more and 0.53 mass % or less, preferably 0.01 mass % or more and 0.4 mass % or less, and more preferably 0.01 mass % or more and 0.3 mass % or less.

The amount of water can be measured using, for example, a commercially available infrared moisture measuring device. Specifically, FD-720 manufactured by Kett Electric Laboratory is exemplified. The amount of water contained in the catalyst is calculated by the following formula. As a matter of course, the method of measuring the amount of water is not limited to this method, and any method may be used as long as it can accurately determine the the amount of water contained in the catalyst.

Amount of water (mass %)=[(Mass of catalyst before drying−mass of catalyst after drying)/mass of catalyst before drying]×100

The temperature and humidity are measured by the Toyama type temperature and humidity meter (JIS Z8806) using two thermometers, which are dry-bulb thermometer and wet-bulb thermometer, and the absolute humidity in the present invention is derived from the temperature table for the psychrometer. For the temperature table for the psychrometer, reference is made to the 79th volume of the scientific chronology of National Astronomical Observatory of Japan.

The catalyst according to the present invention is a catalyst satisfying the amount of water contained in a range of 0.01 mass % or more and 0.53 mass % or less, preferably 0.01 mass % or more and 0.4 mass % or less, and more preferably 0.01 mass % or more and 0.3 mass % or less.

The catalyst according to the present invention is not particularly limit as long as the amount of water contained satisfies a range of 0.01 mass % or more and 0.53 mass % or less, preferably 0.01 mass % or more and 0.4 mass % or less, and more preferably 0.01 mass % or more and 0.3 mass % or less.

The method of adjusting the amount of water contained in the catalyst according to the present invention so as to satisfy the above ranges is not particularly limited, and examples thereof include a method of contacting and holding the catalyst after production with outside air having an absolute humidity of 0.011 kg-$H_2$O/kg-Air or higher for less than 7 hours, and preferably 4 hours or less.

According to the method of adjusting the amount of water contained in the catalyst of the present invention, when the catalyst is contacted with and held at an absolute humidity of 0.011 kg-$H_2$O/kg-Air or higher, it is possible to prevent a significant increase in hygroscopicity, an increase in the amount of water, and deterioration in performance of the catalyst after storage due to the influence by them.

The method for producing acrylic acid by the catalyst according to the present invention may be either a single flow method or a reaction raw material recycling method, and can be performed under known conditions. For example, the reaction is performed by introducing a mixed gas which contains: 2 volume % or more and 10 volume % or less, preferably 3 volume % or more and 9 volume % or less of acrolein as a starting material; 2 volume % or more and 12 volume % or less, preferably 3 volume % or more and 10 volume % or less of molecular oxygen; 0 volume % or more and 40 volume % or less, preferably 5 volume % or more and 35 volume % or less of water vapor; and 28 volume % or more and 93 volume % or less, preferably 35 volume % or more and 86 volume % or less of an inert gas (such as nitrogen and carbon dioxide) and the like, to the catalyst at 200° C. or higher and 400° C. or lower and under a pressure of gauge pressure of 0 kPaG or higher and 200 kPaG or lower at a space velocity (=raw material gas flow rate/apparent capacity of filled catalyst) of 500/hr or more and 3000/hr or less. A gas obtained by oxidizing propylene by a known method may be used as the above mixed gas. In this case, unreacted propylene and other by-products may be mixed.

Example

Hereinafter, a mode for carrying out the present invention will be described in detail by giving specific examples. It goes without saying that the present invention is not limited to the examples without departing from the gist thereof, and it is not limited to the carried catalysts exemplified in the examples nor limited to the carried amounts thereof.

The parts in Examples and Comparative Examples mean parts by mass. In addition, the acrolein yield and acrylic acid yield are defined as follows.

Acrolein yield (mol %)=100×(molar number of acrolein formed)/(molar number of propylene fed)

Acrylic acid yield (mol %)=100×(molar number of acrylic acid formed)/(molar number of propylene fed)

Catalyst Production Example 1

To a mixing tank (A) equipped with a stirring motor, 600 parts of pure water at 95° C. and 16.26 parts of ammonium tungstate were added and stirred. Then, 18.22 parts of ammonium metavanadate and 110 parts of ammonium molybdate were dissolved. Subsequently, 3.88 parts of antimony trioxide was added. 15.56 parts of copper sulfate was dissolved in a mixing tank (B) containing 96 parts of deionized water, and the solution was added to the mixing tank (A) to obtain a slurry solution. The liquid feed amount was adjusted such that the outlet temperature of the spray drier was about 100° C., and the slurry solution obtained above was dried. The granules thus obtained were preliminary calcinated at 350° C. for 5 hours under a flow of air.

Next, the preliminary calcinated granules were ground by a ball mill to obtain powder (hereinafter referred to as preliminary calcinated powder). 300 parts of an alundum carrier having a diameter of 4.5 mm was placed in a tumbling granulator equipped with a bottom plate having a diameter of 23 cm and the bottom plate was rotated at 100 rpm to make the centrifugal acceleration be 1.3 G. While sprinkling 50 parts of a 20 mass % aqueous solution of glycerin, the preliminary calcinated powder obtained above were carried such that the carrying ratio was 30 mass %. The obtained shaped product was calcinated at 390° C. for 5 hours under a flow of air to obtain Catalyst A1. The ratio of the active components of Catalyst A1 was $Mo_{12}V_3W_{1.2}Cu_{1.2}Sb_{0.5}$ when molybdenum was 12.

With respect to Examples 1 to 3 and Comparative Example 1, the storage test, measurement of the amount of water, and the oxidation reaction of Catalyst A1 were performed by the following procedures. The results of Examples 1 to 3 and Comparative Example 1 are shown in Table 1.

(Test for Adjusting Amount of Water)

Catalyst A1 was held in a constant temperature and constant humidity chamber under the varied conditions of absolute humidity and time as shown in Table 1 below. While being held, the catalyst was placed in a metallic container without a lid and kept in contact with the air in the room. In order to study the method for adjusting the amount of water, a test in which the catalyst was held in a polyethylene bag having a thickness of 70 μm was also conducted. Here, the catalyst after holding Catalyst A1 is hereinafter referred to as Catalyst B1.

(Measurement of Amount of Water)

5 g of the catalyst which amount of water was adjusted under various conditions was dried at a temperature of 120° C. using FD-720 manufactured by Kett Electric Laboratory. The drying was completed at a time when mass change at 120° C. fell within 0.05% in 30 seconds, and the amount of water was obtained by the following formula.

Amount of water (mass %)=[(Mass of catalyst before drying−mass of catalyst after drying)/mass of catalyst before drying]×100

(Oxidation Reaction)

As a first stage reactor, a stainless reactor having an inner diameter of 28.4 mm, in which a jacket for flowing alumina powder by air as a heat medium and a thermocouple for measuring the temperature of the catalyst layer were installed at the tube axis, was filled with 68 ml of a catalyst containing molybdenum, bismuth and iron as a carried catalyst, and the reaction bath temperature was set to 320° C.

A gas, in which the fed amounts of propylene, air and water were set such that the raw material molar ratio became propylene:oxygen:nitrogen:water=1:1.7:6.4:3.0, was introduced into an oxidation reactor at a space velocity of 862 h$^{-1}$ to produce a reaction product gas containing acrolein. At this time, the reaction rate of propylene was 97%.

As a second stage reactor, a stainless reactor having an inner diameter of 28.4 mm, in which a jacket for flowing alumina powder by air as a heat medium and a thermocouple for measuring the temperature of the catalyst layer were installed at the tube axis, was filled with 68 ml of Catalyst B1 after holding under the conditions of the test for adjusting the amount of water in Table 1, and the reaction bath temperature was set to 260° C.

A gas, obtained by mixing the whole amount of the reaction product gas from the first stage reactor with the air which flow rate was adjusted so as to have a molar ratio of oxygen to propylene of 0.5 at the inlet of the first stage reactor, was fed to the second stage reactor.

After 20 hours lapse from the start of the reaction under the oxidation reaction conditions of the second stage, quantitative analysis of the reaction product by gas chromatography was performed to determine the yield of acrylic acid at the outlet of the second stage reactor filled with Catalyst B1. The results are shown in Table 1.

TABLE 1

| Test | Holding absolute humidity (kg-H$_2$O/kg-Air) | Holding time (hr.) | Amount of water (mass %) | Acrylic acid yield (mol %) |
| --- | --- | --- | --- | --- |
| — | Immediately after production | | 0.07 | 88.05 |
| Example 1 | 0.011 | 4 | 0.27 | 88.57 |
| Example 2 | 0.016 | 4 | 0.27 | 88.42 |
| Example 3 | 0.021 | 4 | 0.52 | 88.33 |
| Comparative Example 1 | 0.021 | 7 | 0.55 | 86.99 |

From the above Table 1, it was confirmed that in the case where the catalysts of Examples 1 to 3 in which the amount of water was in the range of 0.01 mass % to 0.53 mass %, the yield of acrylic acid was improved.

While the present invention has been described in detail with reference to specific embodiments, it will be apparent to those skilled in the art that various changes and modifications can be made without departing from the spirit and scope of the present invention.

This application is based on Japanese patent application (Japanese Patent Application No. 2016-179885) filed on Sep. 14, 2016, the entirety of which is incorporated by reference. In addition, all references cited herein are incorporated in their entirety.

The invention claimed is:

1. A catalyst for producing acrylic acid having an isopolyacid crystal structure,
wherein an amount of water contained in the catalyst is more than 0.07 mass % and 0.3 mass % or less, and
wherein the composition of active components is represented by the following formula (1):

$$(Mo)_{12}(V)_a(W)_b(Cu)_c(Sb)_d(X)_e(Y)_f(Z)_g(O)_h \qquad (1)$$

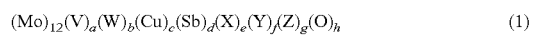

in the formula, Mo, V, W, Cu, Sb, and O represent molybdenum, vanadium, tungsten, copper, antimony and oxygen, respectively; X represents at least one element selected from the group consisting of alkali metals and thallium; Y represents at least one element selected from the group consisting of magnesium, calcium, strontium, barium and zinc; Z represents at least one element selected from the group consisting of niobium, cerium, tin, chromium, manganese, iron, cobalt, samarium, germanium, titanium and arsenic; a, b, c, d, e, f, g and h represent the atomic ratios of respective elements, and with respect to molybdenum atom 12, a represents 0<a≤10, b represents 0≤b≤10, c represents 0<c≤6, d represents 0<d≤10, e represents 0≤e≤0.5, f represents 0≤f≤1, and g represents 0≤g<6; and his the number of oxygen atoms necessary to satisfy the valences of the respective components.

2. A method for producing acrylic acid comprising introducing a mixed gas containing acrolein and molecular oxygen to the catalyst according to claim 1 at a temperature from 200° C. to 400° C.

* * * * *